US 6,544,224 B1

(12) United States Patent
Steese-Bradley

(10) Patent No.: US 6,544,224 B1
(45) Date of Patent: Apr. 8, 2003

(54) LOBED BALLOON CATHETER AND METHOD OF USE

(75) Inventor: Gary W. Steese-Bradley, Los Altos Hills, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/565,773

(22) Filed: May 5, 2000

(51) Int. Cl.[7] .............................................. A61M 37/00
(52) U.S. Cl. .............................. 604/103.06; 604/103.07; 604/103.08; 604/916
(58) Field of Search ........................ 604/96.01, 103.05, 604/103.07, 103.08, 915, 916, 103.06; 606/191, 192, 194

(56) References Cited

U.S. PATENT DOCUMENTS

| 2,078,686 A | * | 4/1937 | Rowe .................... 604/103.08 |
| 3,459,175 A | * | 8/1969 | Miller ................... 604/103.08 |
| 4,141,364 A | * | 2/1979 | Schultze ..................... 604/916 |
| 4,941,877 A | | 7/1990 | Montano, Jr. ................ 604/96 |
| 5,037,392 A | * | 8/1991 | Hillstead .................... 604/916 |
| 5,087,246 A | | 2/1992 | Smith ......................... 604/96 |
| 5,163,989 A | | 11/1992 | Campbell et al. ............. 65/110 |
| 5,195,970 A | | 3/1993 | Gahara ....................... 604/96 |
| 5,207,700 A | * | 5/1993 | Euteneuer ............. 604/103.06 |
| 5,226,887 A | | 7/1993 | Farr et al. .................... 604/96 |
| 5,250,070 A | * | 10/1993 | Parodi .................. 604/103.08 |
| 5,318,587 A | | 6/1994 | Davey ........................ 606/194 |
| 5,320,634 A | * | 6/1994 | Vigil et al. ............. 604/103.08 |
| 5,336,234 A | * | 8/1994 | Vigil et al. ............. 604/103.08 |
| 5,350,361 A | | 9/1994 | Tsukashima et al. .......... 604/96 |
| 5,397,307 A | | 3/1995 | Goodin ........................ 604/96 |
| 5,456,666 A | | 10/1995 | Campbell et al. ............. 604/96 |
| 5,458,572 A | | 10/1995 | Campbell et al. ............. 604/96 |
| 5,478,319 A | * | 12/1995 | Campbell et al. ....... 604/103.08 |
| 5,490,839 A | | 2/1996 | Wang et al. .................. 604/96 |
| 5,496,276 A | | 3/1996 | Wang et al. .................. 604/96 |
| 5,718,684 A | | 2/1998 | Gupta ......................... 604/96 |
| 5,738,901 A | | 4/1998 | Wang et al. .................. 427/2.3 |
| 5,746,745 A | * | 5/1998 | Abele et al. ............ 604/103.08 |
| 5,792,172 A | | 8/1998 | Fischell et al. ............... 606/198 |
| 5,792,300 A | | 8/1998 | Inderbitzen et al. ... 156/244.13 |
| 5,902,268 A | | 5/1999 | Saab .......................... 604/96 |
| 5,954,740 A | | 9/1999 | Ravenscroft et al. ........ 606/194 |
| 6,013,055 A | | 1/2000 | Bampos et al. ............... 604/96 |
| 6,033,380 A | | 3/2000 | Butaric et al. ................ 604/96 |

FOREIGN PATENT DOCUMENTS

| EP | 0 737 488 A1 | 10/1996 |
| FR | 2 529 083 | 12/1983 |
| WO | WO 97/25093 | 12/1996 |

* cited by examiner

Primary Examiner—Teresa Walberg
Assistant Examiner—Fadi H. Dahbour
(74) Attorney, Agent, or Firm—Fulwider Patton Lee & Utecht, LLP

(57) ABSTRACT

A balloon catheter with a balloon having at least a section which has an uninflated configuration with at least two lobes and an inflated configuration with a cylindrical surface. In a presently preferred embodiment, the balloon has a lobed inner surface and a lobed outer surface. In one embodiment, the balloon has a uniform wall thickness around a circumference of the lobed balloon section. However, in alternative embodiments the balloon wall thickness may nonuniform around the balloon circumference. Each lobe forms a deflated balloon wing when the balloon is deflated.

26 Claims, 4 Drawing Sheets

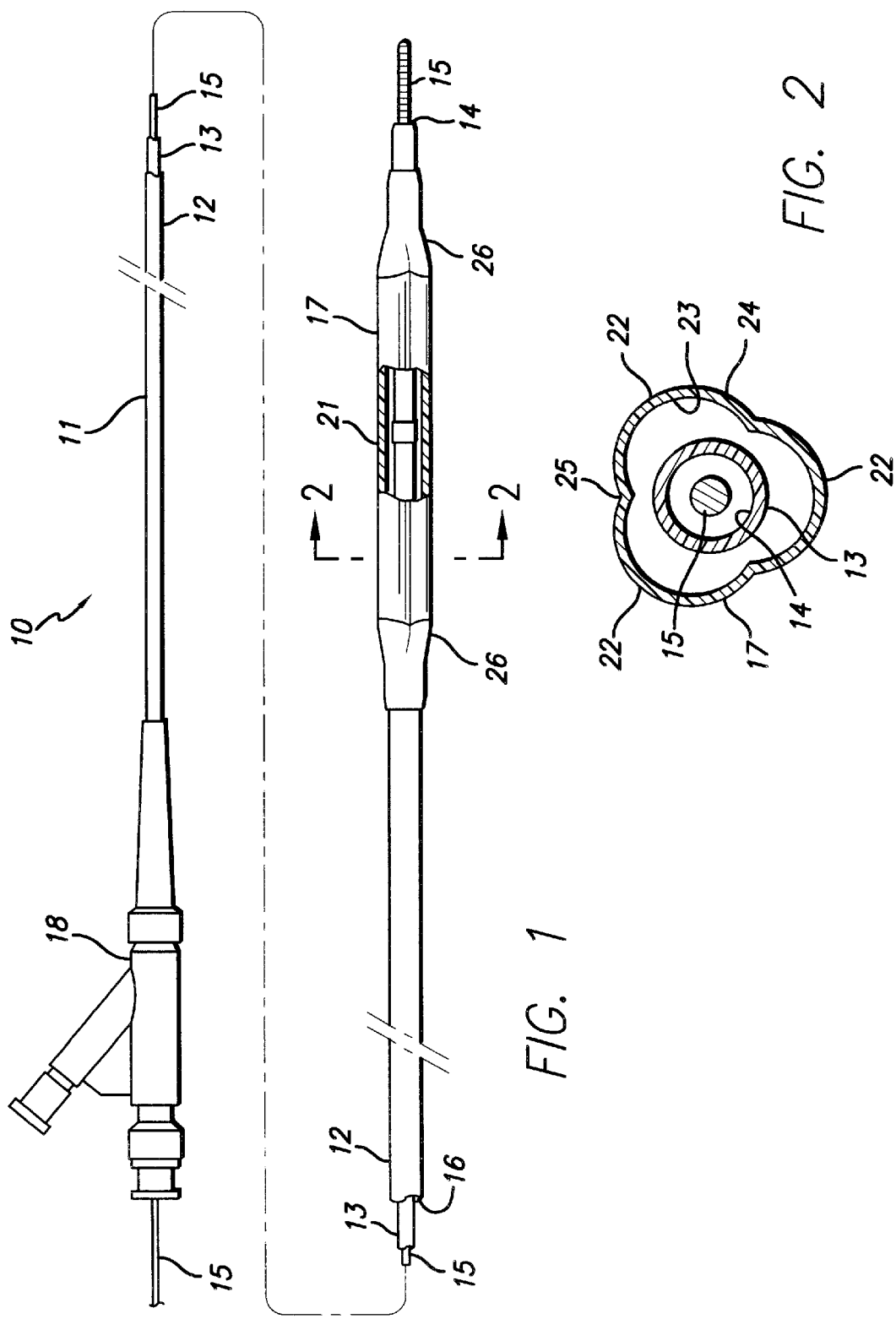

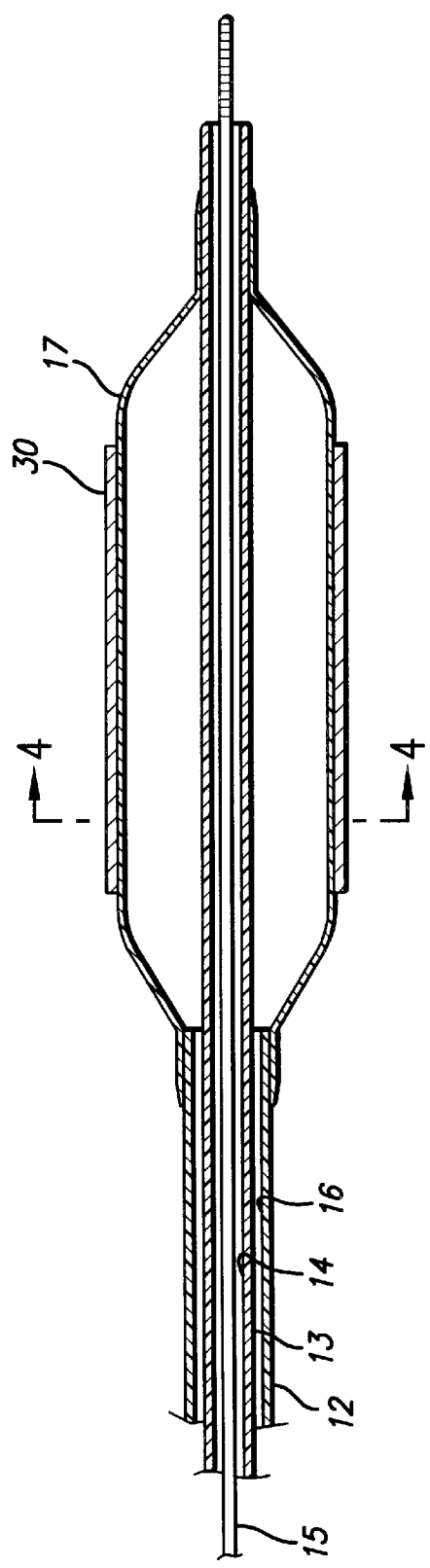
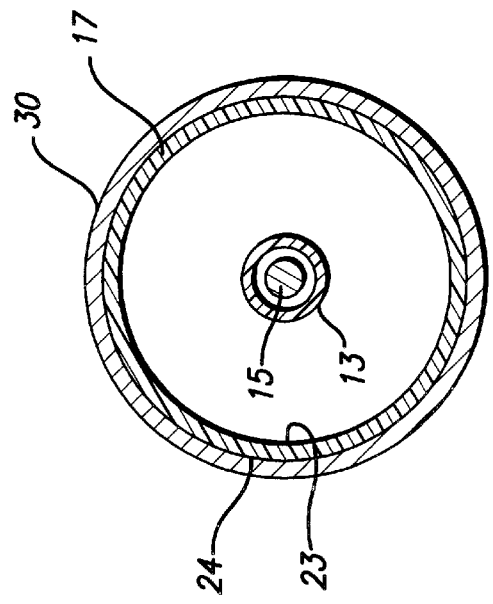

LOBED BALLOON CATHETER AND METHOD OF USE

BACKGROUND OF THE INVENTION

This invention relates to the field of medical devices, and more particularly to a balloon catheter having a lobed balloon.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter, and the stent is left in place within the artery at the site of the dilated lesion.

In the design of catheter balloons, balloon characteristics such as strength, flexibility and compliance must be tailored to provide optimal performance for a particular application. Angioplasty balloons preferably have high strength for inflation at relatively high pressure, and high flexibility and softness for improved ability to track the tortuous anatomy and cross lesions. The balloon compliance is chosen so that the balloon will have a desired amount of expansion during inflation. Compliant balloons, for example balloons made from materials such as polyethylene, exhibit substantial stretching upon the application of tensile force. Noncompliant balloons, for example balloons made from materials such as PET, exhibit relatively little stretching during inflation, and therefore provide controlled radial growth in response to an increase in inflation pressure within the working pressure range.

In order to decrease the cross sectional profile of the balloon catheter to thereby facilitate advancement of the catheter within the patient's vasculature and across a stenosed region, balloons may be folded into a low profile configuration having balloon wings wrapped around the balloon prior to insertion into the patient. However, one difficulty has been after the balloon is inflated in the patient and subsequently deflated, the balloon tends to form a large flat wing or a bunched up irregular shape. The resulting relatively large profile of the deflated balloon tends to complicate repositioning or removal of the balloon in the vasculature.

It would be a significant advance to provide a catheter balloon with improved refold after inflation of the balloon.

SUMMARY OF THE INVENTION

The invention is directed to a balloon catheter including an elongated shaft, and a balloon on a distal shaft section having at least a section which has an uninflated configuration or partially inflated with at least two lobes, and which has an inflated configuration with a cylindrical surface. In a presently preferred embodiment, the balloon has a lobed inner surface and a lobed outer surface. In one embodiment, the balloon has a uniform wall thickness around a circumference of the lobed balloon section. However, in alternative embodiments the balloon wall thickness may be nonuniform around the balloon circumference. Each lobe forms a wing when the balloon is deflated. The deflated wings provide a deflated balloon with a relatively low profile, which facilitates advancement of the catheter balloon across a stenosis and the repositioning or removal of the balloon catheter within the patient's vasculature.

The lobed balloon section preferably extends at least the length of the working length of the balloon, and in one embodiment, the lobed section includes at least a portion of the tapers at one or both ends of the working length of the balloon. Additionally, in one embodiment, the lobed section includes a stepped, smaller diameter section proximal and/or distal to the working length. The lobes are disposed around the circumference of the balloon. The lobes may have a variety of suitable shapes, such that the lobes preferentially collapse during deflation of the balloon to each form a deflated wing. In a presently preferred embodiment, each lobe has a curved or cylindrical shape. In an alternative embodiment, the lobes have an angled configuration such as a triangular shape.

In a presently preferred embodiment, the balloon has about 2 to about 10 lobes, and preferably at least three lobes. The number of lobes depends on the inflated diameter of the balloon within the working pressure range of the balloon. Specifically, larger diameter balloons will preferably have a greater number of lobes than a smaller diameter balloon, to thereby form a greater number of deflated wings. By increasing the number of deflated wings, the overall size of each wing is reduced to a point where the deflated balloon profile is sufficiently low. In a presently preferred embodiment, a balloon having a 3.0 mm inflated working outer diameter has three lobes, and a balloon having a 4.0 to 6.0 mm inflated working outer diameter has four to six lobes. However, the number of lobes will depend on the desired performance of the balloon, so that larger diameter balloon having an inflated working outer diameter of greater than 3.0 mm may have as little as 2 or 3 lobes.

The balloon inflates into a cylindrical shape, which in a presently preferred embodiment forms when any substantial inflation pressure above atmospheric pressure is applied inside the balloon. Thus, the lobes are not identifiable when the balloon is inflated at elevated pressure, but are identifiable on the balloon when the balloon is at or near atmospheric pressure. The balloon is inflated to the cylindrical inflated configuration to perform a procedure such as dilatating a lesion, implanting a stent, or post-dilatation touch-up in the patient's blood vessel.

In a presently preferred embodiment, the balloon is formed in a mold having the lobed shape. Thus, a polymeric tube is placed in the mold and inflated therein, generally at elevated temperatures, to form the balloon having the lobed shape. The polymeric tube may be configured to provide a balloon with substantially uniform or nonuniform wall thickness. As a result of being expanded in the mold, both the outer surface of the balloon and the inner surface of the balloon develop the lobed shape. Consequently, the balloon consistently deflates with wings formed by each lobe during removal of the inflation fluid from the balloon, and without the need to hold the interior of the balloon under vacuum after removal of the inflation fluid therefrom to force the wings to form. Additionally, the rupture and compliance characteristics of the balloon can be made uniform around the circumference of the balloon due to the uniform nature of the balloon wall.

The balloon of the invention provides excellent ability to cross stenosed or otherwise narrow regions of the patient's vasculature, and deflates to a low profile configuration due to the uninflated configuration having lobes which form deflated wings. Additionally, the balloon inflates easily to a desired cylindrical cross section. These and other advantages of the invention will become more apparent from the following detailed description of the invention and the accompanying exemplary drawings.

BRIEF DESCRIPTION OF THE DRAWINGS

FIG. 1 is an elevational view, partially in section, of a balloon catheter which embodies features of the invention, illustrating the balloon in an uninflated configuration with lobes.

FIG. 2 is a transverse cross sectional view of the balloon shown in FIG. 1, taken along line 2—2.

FIG. 3 is an enlarged longitudinal cross sectional view of a distal portion of the balloon catheter shown in FIG. 1, illustrating the balloon in an inflated configuration.

FIG. 4 is a transverse cross sectional view of the balloon shown in FIG. 3, taken along line 4—4.

DETAILED DESCRIPTION OF THE INVENTION

Figure 7:
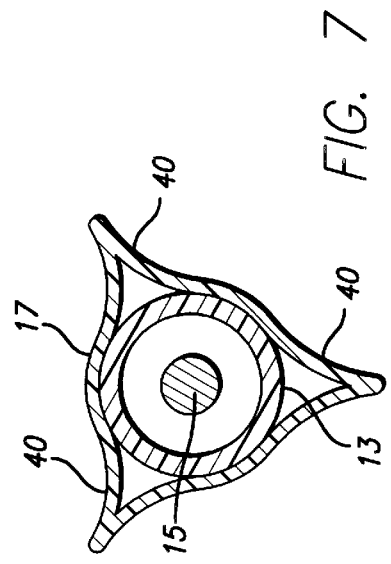
FIG. 7 is a transverse cross sectional view of the balloon catheter shown in FIG. 1, illustrating the balloon in a deflated configuration with wings.

FIG. 1 illustrates a balloon catheter 10 which embodies features of the invention. Catheter 10 generally comprises an elongated catheter shaft 11 having an outer tubular member 12 and an inner tubular member 13 disposed within outer tubular member 12. Inner tubular member 13 defines a guidewire lumen 14 adapted to slidingly receive a guidewire 15. The coaxial relationship between outer tubular member 12 and inner tubular member 13 defines annular inflation lumen 16. An inflatable balloon 17 is disposed on a distal section of catheter shaft 11, having a proximal end sealingly secured to the distal end of outer tubular member 12 and a distal end sealingly secured to the distal end of inner tubular member 13 so that its interior is in fluid communication with inflation lumen 16. An adapter 18 at the proximal end of catheter shaft 11 is configured to direct inflation fluid into inflation lumen 16 and to provide access to guidewire lumen 14.

FIG. 1 illustrates balloon 17 in an uninflated configuration, i.e., at atmospheric pressure. Balloon 17 has a working length 21 having an uninflated configuration with three lobes 22 (FIG. 2). As best illustrated in FIG. 2, showing a transverse cross section of the balloon catheter shown in FIG. 1, taken along line 2—2, each lobe 22 is circumferentially displaced around the balloon 17 from adjacent lobes 22, and the balloon working length 21 has an inner lobed surface 23 and an outer lobed surface 24. Thus, in the uninflated configuration, the inner and outer surfaces 23/24 of the balloon working length 21 have an irregular shape corresponding to the shape of the lobes, and do not have a cylindrical shape. In a presently preferred embodiment, the lobed section of the balloon extends beyond the ends of the working length 21 of the balloon 17 to the tapered region 26 of the balloon on either end of the working length. However, in alternative embodiments, the lobed section does not extend beyond the working length 21 of the balloon 17. In one embodiment, the balloon has a stepped profile when inflated, in which the balloon has a first tapered section which tapers from the proximal end of the working length to a proximal inflatable smaller diameter section located proximal to the working length, and/or a second tapered section at the distal end of the working length which tapers to a distal inflatable smaller diameter section located distal to the working length (not shown). The smaller diameter proximal and distal sections are preferably longitudinally aligned with the working length, but inflate to a smaller diameter of the working length. The balloon has third and fourth tapered sections which taper from the smaller diameter proximal and distal sections, respectively, to the shaft section of the balloon secured to the catheter shaft. In a presently preferred embodiment, the lobed sections of the balloon include at least the smaller diameter proximal and distal sections of the balloon, and preferably extend to the proximal end of the third tapered section and to the distal end of the fourth tapered section.

In the embodiment illustrated in FIG. 2 having three balloon lobes 22, the balloon 17 has three longitudinally extending sections 25 where adjacent lobes 22 meet, forming a junction between adjacent lobes 22. In the uninflated configuration, the balloon interior has a radius at the longitudinally extending sections 25 which is less than a radius of the balloon interior between the longitudinally extending sections. The balloon deflates so that the sections 25 forming the junctions between lobes 22 are preferentially drawn inwardly toward the balloon center, and the sides of a lobe 22 are drawn together to form a wing.

FIG. 3 illustrates a distal portion of the balloon catheter 10 shown in FIG. 1, with the balloon 17 in an inflated configuration. Balloon 17 has an inflated configuration with a cylindrical inner surface 23 and a cylindrical outer surface 24, as shown in FIG. 4, illustrating a transverse cross section of the balloon catheter 10 shown in FIG. 3, taken along line 4—4. In the embodiment illustrated in FIG. 3, an expandable stent 30 is mounted on balloon 17. Stent 30 would typically be mounted on the working length 21 of the uninflated balloon 17 prior to introduction of the catheter 10 into the patient. The distal end of catheter 10 may be advanced to a desired region of a patient's lumen in a conventional manner, and balloon 17 may be inflated to expand stent 30, seating it in the lumen. The balloon 17 is deflated, so that lobes 22 form deflated wings, and the balloon catheter 10 may be repositioned for another procedure or removed from the body lumen.

Figure 5:
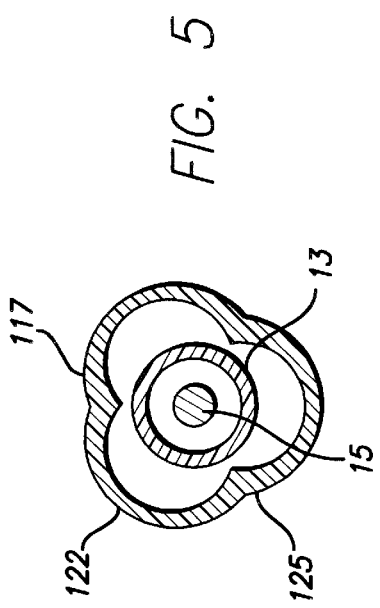
FIG. 5 is a transverse cross sectional view of an alternative configuration of a balloon catheter which embodies features of the invention, having a balloon with a nonuniform wall thickness, illustrating the balloon in an uninflated configuration.
Figure 6:
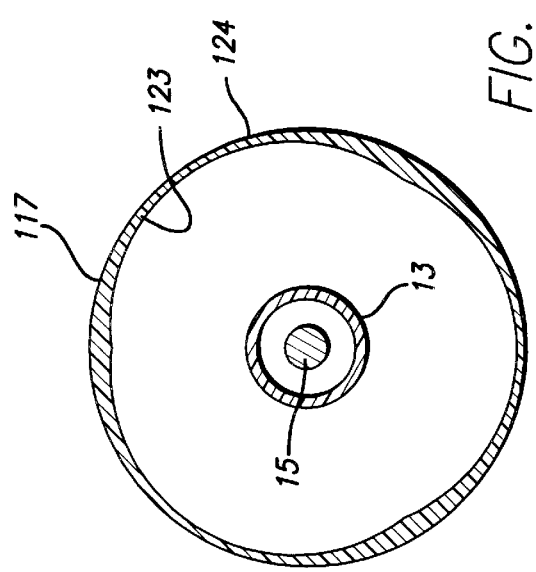
FIG. 6 is a transverse cross sectional view of the alternative configuration of a balloon catheter shown in FIG. 5, illustrating the balloon in an inflated configuration.

In the embodiment illustrated in FIG. 1, the balloon working length 21 has a uniform wall thickness around the circumference of the balloon. In one embodiment, the balloon 17 illustrated in FIG. 1 having a uniform wall thickness is formed from a uniform wall thickness parison. The term "uniform" as it is applied to the wall thickness of the balloon working length 21 should be understood to include the slight variations in wall thickness typically found in catheter cylindrical balloons. For example, the variations in the double wall thickness of a conventional 3.0 mm outer diameter balloon are typically about 0.0002 to about 0.0005 inches, preferably about 0.0003 to about 0.0004 inches. An alternative embodiment having a nonuniform wall thickness is illustrated in FIGS. 5 and 6. FIG. 5 illustrates balloon 117 in an uninflated configuration with three lobes 122. Balloon 117 has three longitudinally extending sections 125 where adjacent lobes 122 meet, forming a junction between adjacent lobes 122. The longitudinally extending sections 125 have a wall thickness which is greater than a wall thickness of the balloon working length 121 located between the longitudinally extending sections 125. In the embodiment illustrated in FIG. 5, similar to balloon 17, balloon 117 deflates so that the thicker walled sections 125 forming the junction between adjacent lobes 122 preferentially collapses inwardly toward the balloon center and the sides of a lobe 122 are drawn together to form a wing. FIG. 6 illustrates the balloon 117 in an inflated configuration, having a cylindrical outer surface 124. In the embodiment illustrated in FIG. 6, the inner surface 123 of the balloon working length 121 has a nonuniform shape due to the nonuniform wall thickness. Factors such as the parison shape and the size of the differential between the outer diameter of the balloon at the lobe and the outer diameter of the balloon between two lobes in the uninflated configuration will affect whether the balloon 17 having a working length 21 with a uniform working length, or the balloon 117 having a working length 121 with a nonuniform wall thickness is produced. Except as otherwise stated, the discussions herein relating to balloon 17 should be understood to apply to balloon 117 as well.

Figure 8:
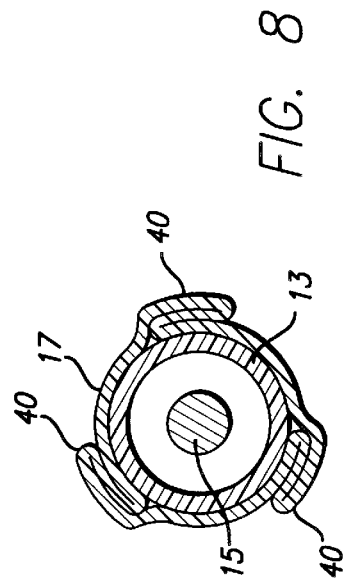
FIG. 8 illustrates the balloon shown in FIG. 7 with the wings wrapped around the catheter shaft.

FIG. 7 illustrates the balloon 17 in a deflated configuration, with the lobes 22 forming deflated wings 40. When inflation medium is removed from the balloon, the three lobes 22 collapse to form three wings 40. The three wings 40 provide a lower profile than would be present if the balloon deflated to form one or two larger wings. To form the deflated configuration, the physician typically removes the inflation fluid in the balloon by drawing the fluid out with an indeflator or syringe. Following removal of the inflation fluid, the balloon interior is typically held under vacuum. In the deflated configuration, catheter 10 may be repositioned or removed from the patient's body lumen, which typically involves withdrawing the catheter 10 into a guiding catheter (not shown), and wings 40 provide a low profile configuration that facilitates this procedure. FIG. 8 illustrates the balloon after the wings 40 have been wrapped around the shaft 11 in preparation for introducing the catheter into the patient. As illustrated in FIG. 8, lobes of the balloon produce a winged balloon wherein the low profile of the winged balloon provides improved ability to cross stenosed and otherwise narrow regions of the patient's vasculature.

Figure 10:
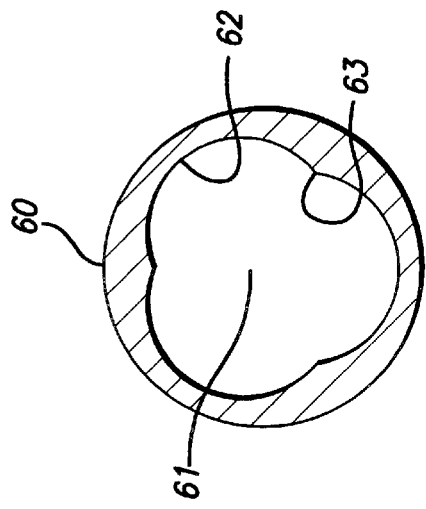
FIG. 10 is a transverse cross sectional view of an alternative mold useful in forming a balloon which embodies features of the invention.
Figure 9:
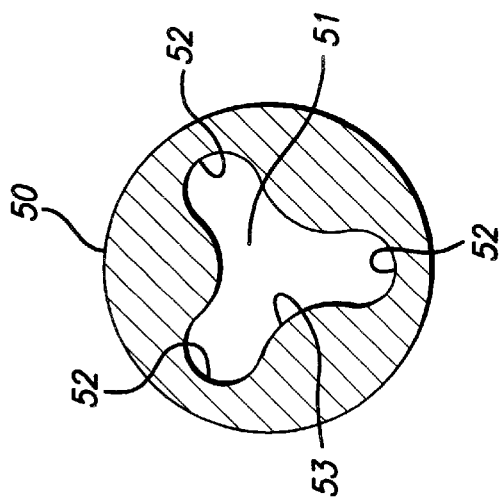
FIG. 9 is a transverse cross sectional view of a mold useful in forming a balloon which embodies features of the invention.

FIG. 9 illustrates a transverse cross section of a balloon mold 50, useful in forming a balloon which embodies features of the invention. In the embodiment shown in FIG. 9, the mold has an inner cavity 51 with three lobes 52 having concave surfaces. The inner cavity 51 has rounded sections 53 with convex surfaces between the lobes 52. Lobes 52 in the mold 50 form lobes 22 of balloon 17, and sections 53 in the mold 50 form the longitudinally extending sections 25 of balloon 17. FIG. 10 illustrates a transverse cross section of another embodiment of a balloon mold 60, useful in forming a balloon which embodies features of the invention, having an inner cavity 61 and three lobes 62 with concave surfaces. The mold 60 differs from the mold 50 in that concave surfaces of the lobes 62 directly meet to define the sections 63 between the lobes 62. A polymeric tubular member is placed in the mold 50/60 and expanded, typically at elevated temperature and pressure, and optionally under axially tension, to form the balloon. To prepare the balloon 17, the mold used to form the balloon has a radius of about 0.03 to about 0.2 inches, and more specifically about 0.045 to about 0.15 inches from the center of the mold to the inner surface of the mold at the midpoint of a lobe 52/62, and a radius of about 0.01 to about 0.1 inches, more specifically about 0.02 to about 0.055 inches from the center of the mold to the inner surface of the mold at the midpoint of section 53/63 between two lobes, depending on the desired outer diameter of the balloon, which is typically about 1.5 to about 6.0 mm.

Figure 11:
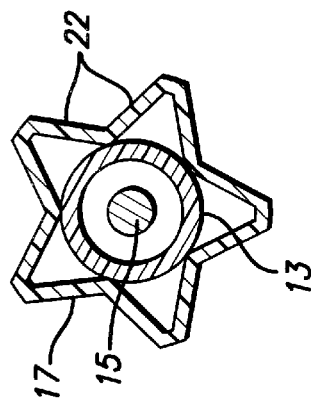
FIG. 11 is a transverse cross sectional view of a balloon catheter which embodies features of the invention, with a balloon having a star shaped cross section with triangular lobes, illustrating the balloon in an uninflated configuration.

In the embodiment illustrated in FIG. 2, the lobes 22 comprise rounded projecting balloon portions. The round lobes 22 illustrated in FIG. 2 provide improved refold to a low profile winged shape, easy inflation to the cylindrical inflated configuration, and ease of manufacture. However, a variety of suitable shapes may be used for lobes 22. In the embodiment illustrated in FIG. 11, the lobes 22 are triangular, and form a five lobed, star-shaped balloon.

In a presently preferred embodiment, the material forming the balloon 17 is uniform, i.e., sections of the balloon are not formed of different material. Thus, the material forming the lobed section of the balloon is the same around the circumference of the balloon and the lobes are formed of the same material. The balloon can be formed from a variety of suitable polymeric materials commonly used to form catheter balloons, including polyamides such as nylon, polyether block amides (PEBAX), polyurethane, polyurethane copolymers such as PELLETHANE, polyesters, and blends thereof.

In the embodiment illustrated in FIG. 1, the interior of balloon 17 does not form separately inflatable interior chambers. Thus, the lobes 22 form a common balloon interior in fluid communication with inflation lumen 16. In alternative embodiments, the elongated shaft 11 may have multiple separate inflation lumens, and balloon 17 may have multiple interior chambers therein (not shown).

The dimensions of catheter 10 are determined largely by the size of the guidewires to be employed and the size of the artery or other body lumen through which the catheter must pass or the size of the stent being delivered. Typically, the outer tubular member 12 has an outer diameter of about 0.02 to about 0.04 inch (0.05 to 0.10 cm), usually about 0.037 inch (0.094 cm), an inner diameter of about 0.015 to about 0.035 inch (0.038 to 0.089 cm), usually about 0.03 inch (0.076 cm). The wall thickness of the outer tubular member 12 can vary from about 0.002 to about 0.008 inch (0.0051 to 0.0201 cm), typically about 0.003 inch (0.0076 cm). The inner tubular member 13 typically has an outer diameter of about 0.012 to about 0.016 inch (0.030 to 0.041 cm), usually about 0.014 inch (0.036 cm). The overall working length of the catheter 10 may range from about 90 to about 160 cm, and is typically about 135 cm. Preferably, balloon 17 may have a length about 0.5 cm to about 4 cm and typically about 2 cm with an inflated working diameter of about 1 to about 10 mm, at inflation pressures of generally about 6 to about 16 atmospheres.

The balloon catheter illustrated in FIG. 1 is an over-the-wire catheter. However, various balloon catheter designs may be used, such as rapid exchange and fixed wire catheters. Rapid exchange catheters typically have an elongated shaft with a proximal end, a distal end with a balloon on a distal shaft section in fluid communication with an inflation lumen, a distal port in the distal end of the catheter, a proximal port spaced a substantial distance from the proximal end of the catheter closer to the distal end than to the proximal end, and a short guidewire lumen extending between the proximal and distal ports. The balloon 17 may be configured for a variety of different uses, as for example as a dilatation balloon, stent delivery balloon, or radiation delivery catheter balloon.

The invention has been discussed in terms of certain preferred embodiments. One of skill in the art will recognize that various modifications may be made without departing from the scope of the invention. For example, while discussed primarily in terms lobes on the working length of the balloon, the lobes could alternatively be located on other balloon sections such as stepped smaller diameter sections of the balloon located proximal and/or distal to the working length. Moreover, while certain features may be shown or discussed in relation to a particular embodiment, such individual features may be used on the various other embodiments of the invention.

What is claimed is:

1. A balloon catheter, comprising:
   an elongated shaft having a proximal end, a distal end, and an inflation lumen; and
   a balloon on a distal shaft section having an interior in fluid communication with the inflation lumen, and having at least a section which has an uninflated configuration with at least two lobes, each with a concave inner surface and a concave outer surface, and which has an inflated configuration with a cylindrical surface;
   wherein each lobe has edges in contact with edges of adjacent lobes.

2. The balloon catheter of claim 1 wherein the balloon section has a uniform wall thickness around a circumference thereof.

3. The balloon catheter of claim 1 wherein the balloon section has longitudinally extending sections along a junction between adjacent lobes having a wall thickness which is greater than a wall thickness of the balloon section located between the longitudinally extending sections.

4. The balloon catheter of claim 1 wherein the inflated configuration has a cylindrical inner surface.

5. The balloon catheter of claim 1 wherein the inflated configuration has a cylindrical outer surface.

6. The balloon catheter of claim 1 wherein the lobes define a common balloon interior.

7. The balloon catheter of claim 1 wherein the lobes are formed of the same material.

8. The balloon catheter of claim 1 wherein a material forming the section of the balloon is the same around a circumference of the balloon.

9. The balloon catheter of claim 1 wherein the section of the balloon is a working length, and the inflated configuration is formed at an inflation pressure at least within a working pressure range of the balloon.

10. The balloon catheter of claim 1 wherein the section of the balloon is a working length, and the inflated configuration is formed at an inflation pressure below a working pressure range of the balloon.

11. The balloon catheter of claim 1 having three to ten lobes.

12. The balloon catheter of claim 1 wherein the lobes are round.

13. The balloon catheter of claim 1 wherein each lobe forms a deflated balloon wing.

14. A balloon catheter, comprising:
   an elongated shaft having a proximal end, a distal end, and an inflation lumen; and
   a balloon on a distal shaft section having an interior in fluid communication with the inflation lumen, and having at least a section which has an uninflated configuration and at least two lobes, each with a concave inner surface and a concave outer surface and which has an inflated configuration with a cylindrical surface;
   wherein the balloon section has longitudinally extending sections along a junction between adjacent lobes having a wall thickness which is greater than a wall thickness of the balloon section located between the longitudinally extending sections.

15. A balloon for a catheter, comprising a working length having an uninflated configuration with at least two lobes each with a concave inner surface and a concave outer surface, and having an inflated configuration with a cylindrical surface
   wherein the balloon section has longitudinally extending sections along a junction between adjacent lobes having a wall thickness which is greater than a wall thickness of the balloon section located between the longitudinally extending sections.

16. The balloon of claim 15 wherein the inflated configuration has a cylindrical inner surface.

17. The balloon of claim 15 wherein the inflated configuration has a cylindrical outer surface.

18. A method of performing a medical procedure, comprising:
   a) positioning within a body lumen a balloon catheter, comprising
      i) an elongated shaft having a proximal end, a distal end, and an inflation lumen; and
      ii) a balloon on a distal shaft section having an interior in fluid communication with the inflation lumen, having at least a section which has an uninflated configuration with at least two lobes each with a concave inner surface and a concave outer surface, and which has an inflated configuration with a cylindrical surface;

b) inflating the balloon from the uninflated lobed configuration to the inflated cylindrical configuration within the body lumen; and c) deflating the balloon to the uninflated lobed configuration within the body lumen, so that each lobe forms a deflated balloon wing.

19. The method of claim 18 wherein the inflated configuration of the balloon has a cylindrical outer surface, and including inflating the balloon to dilate a stenosed region of the body lumen.

20. The method of claim 18 wherein the balloon has a stent mounted thereon, and including inflating the balloon to expand the stent to an expanded cylindrical configuration.

21. A balloon catheter, comprising:

an elongated shaft having a proximal end, a distal end, and an inflation lumen; and a balloon on a distal shaft section having an interior in fluid communication with the inflation lumen, and having at least a section which has an uninflated configuration with at least two lobes, each with a concave inner surface and a concave outer surface, and which has an inflated configuration with a cylindrical surface;

wherein the balloon section has longitudinally extending sections along a junction between adjacent lobes having a wall thickness which is greater than a wall thickness of the balloon section located between the longitudinally extending sections.

22. A balloon catheter, comprising:

an elongated shaft having a proximal end, a distal end, and an inflation lumen; and a balloon on a distal shaft section having an interior in fluid communication with the inflation lumen, and having at least a section which has an uninflated configuration with at least two lobes, each with a concave inner surface and a concave outer surface, and which has an inflated configuration with a cylindrical surface;

wherein each lobe forms a deflated balloon wing.

23. A balloon catheter, comprising:

an elongated shaft having a proximal end, a distal end, and an inflation lumen; and a balloon on a distal shaft section having an interior in fluid communication with the inflation lumen, and having at least a section which has an uninflated and at least two lobes, each with a concave inner surface and a concave outer surface and which has an inflated configuration with a cylindrical surface;

wherein each lobe has edges in contact with edges of adjacent lobes.

24. A balloon catheter, comprising:

an elongated shaft having a proximal end, a distal end, and an inflation lumen; and a balloon on a distal shaft section having an interior in fluid communication with the inflation lumen, and having at least a section which has an uninflated and at least two lobes, each with a concave inner surface and a concave outer surface and which has an inflated configuration with a cylindrical surface;

wherein each lobe forms a deflated balloon wing.

25. A balloon for a catheter, comprising a working length having an uninflated configuration with at least two lobes each with a concave inner surface and a concave outer surface, and having an inflated configuration with a cylindrical surface;

wherein each lobe has edges in contact with edges of adjacent lobes.

26. A balloon for a catheter, comprising a working length having an uninflated configuration with at least two lobes each with a concave inner surface and a concave outer surface, and having an inflated configuration with a cylindrical surface;

wherein each lobe forms a deflated balloon wing.

* * * * *